(12) United States Patent
Zitt et al.

(10) Patent No.: US 10,115,484 B2
(45) Date of Patent: *Oct. 30, 2018

(54) TRACKING MEDICATION INVENTORY USING ONE OR MORE LINKED PRESSURE SENSORS

(71) Applicant: PAZIPRO LLC, Nashville, TN (US)

(72) Inventors: Patrick Zitt, Knoxville, TN (US); James Protich, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,047

(22) Filed: May 18, 2017

(65) Prior Publication Data
US 2018/0130550 A1    May 10, 2018

Related U.S. Application Data

(63) Continuation-in-part of application No. 14/991,068, filed on Jan. 8, 2016, now Pat. No. 9,715,801.

(60) Provisional application No. 62/102,293, filed on Jan. 12, 2015.

(51) Int. Cl.
| | |
|---|---|
| *G08B 13/14* | (2006.01) |
| *G16H 20/10* | (2018.01) |
| *A61J 7/04* | (2006.01) |
| *G08B 21/18* | (2006.01) |

(52) U.S. Cl.
CPC .............. *G16H 20/10* (2018.01); *A61J 7/04* (2013.01); *G08B 21/182* (2013.01); *A61J 2200/74* (2013.01); *A61J 2205/10* (2013.01)

(58) Field of Classification Search
CPC ......... G16H 20/10; G08B 21/182; A61J 7/04; A61J 2200/74; A61J 2205/10
See application file for complete search history.

(56) References Cited

U.S. PATENT DOCUMENTS

| | | | | |
|---|---|---|---|---|
| 2002/0059833 | A1* | 5/2002 | Imai | G01L 19/0007 73/715 |
| 2005/0093690 | A1* | 5/2005 | Miglionico | G01G 3/12 340/539.1 |
| 2005/0177136 | A1* | 8/2005 | Miller | A61M 5/145 604/890.1 |
| 2006/0099971 | A1* | 5/2006 | Staton | G08C 17/00 455/456.6 |

(Continued)

*Primary Examiner* — Erin M File
(74) *Attorney, Agent, or Firm* — Matthew M. Googe; Robinson IP Law, PLLC (57) ABSTRACT

A system for tracking an inventory of medication includes: one or more medication detecting devices, each of the medication detecting devices having a medication container for receiving medication; a pressure sensing component in sensory contact with the medication portion; one or more personal communication devices; a remote database in communication with the one or more pressure sensors and the at least one personal communication device; an interactive user interface displayed on the display of the personal communication device for receiving medication data from a user. When one of the pressure sensors detects a pressure change on the pressure sensing component, the detected change of pressure is transmitted to the remote database, wherein the remote database analyzes the change in pressure from the one or more pressure sensors and transmits an alert when the detected pressure change corresponds to the medication input parameters inputted by the user.

3 Claims, 8 Drawing Sheets

(56) References Cited

U.S. PATENT DOCUMENTS

| | | | |
|---|---|---|---|
| 2006/0271112 A1* | 11/2006 | Martinson | A61B 5/0031 607/2 |
| 2007/0017506 A1* | 1/2007 | Bell | A61M 15/009 128/200.23 |
| 2010/0203227 A1* | 8/2010 | Arp | G01K 1/024 427/2.14 |
| 2011/0057796 A1* | 3/2011 | Candelore | G08B 25/14 340/565 |
| 2011/0187549 A1* | 8/2011 | Balasingam | A47B 81/00 340/687 |
| 2012/0322380 A1* | 12/2012 | Nannarone | G08B 13/1427 455/41.2 |
| 2014/0253321 A1* | 9/2014 | Srinivasan | G08B 13/00 340/539.11 |
| 2014/0266710 A1* | 9/2014 | Nguyen | H04M 1/00 340/539.13 |
| 2015/0102924 A1* | 4/2015 | Soloway | G08B 25/008 340/539.11 |
| 2017/0325685 A1* | 11/2017 | Shachar | A61B 5/0031 |

* cited by examiner

TRACKING MEDICATION INVENTORY USING ONE OR MORE LINKED PRESSURE SENSORS

CROSS-REFERENCES TO RELATED APPLICATIONS

This application claims priority to and is a continuation-in-part of U.S. patent application Ser. No. 14/991,068 for a System and Method of Object Tracking Using a Plurality of Linked Pressure Sensors filed on Jan. 8, 2016, which claims priority to U.S. Provisional Patent Application No. 62/102,293 for a System of Linked Pressure Sensors, which was filed on Jan. 12, 2015, the contents of which are incorporated herein by reference in their entireties.

FIELD

This disclosure relates to the field of medication monitoring. More particularly, this disclosure relates to a system including one or more pressure sensors for determining an amount of available medication.

BACKGROUND

Various medication systems are available that detect medication. However, these systems are limited and may only provide limited alerting abilities or customization of alerts by a user.

What is needed, therefore, is a system and method of tracking medication using one or more pressure sensors for determining an amount of medication available and enabling a customized alert to be sent to one or more users based on medication amount.

SUMMARY

A system and method of tracking medication using one or more pressure sensors for determining an amount of medication available is provided. In a first aspect, a system for tracking an inventory of medication includes: one or more medication detecting devices, each of the medication detecting devices having a medication container for receiving a first amount of a medication, a pressure sensing component in sensory contact with the medication portion for measuring a pressure applied by the first amount of medication on the medication portion, an embedded processor in electronic communication with the pressure sensing component and a sensor communication module; one or more personal communication devices, the one or more personal communication devices having a display, at least one computer readable storage medium, a device communication module for transmitting and receiving data; and a processor in communication with the display, the at least one computer readable storage medium, and the device communication module; a remote database in communication with the one or more pressure sensors and the at least one personal communication device via the sensor communication module of the one or more pressure sensors and the device communication module of the personal communication device, the remote database including a processor and one or more computer readable storage mediums; an interactive user interface displayed on the display of the personal communication device for receiving one or more medication parameters from a user corresponding to a change in pressure detected by the pressure sensing component of each of the one or more pressure sensors and for displaying information related to the one or more pressure sensors. When one of the one or more pressure sensors detects a pressure change on the pressure sensing component, the detected change of pressure is transmitted to the remote database, wherein the processor of the remote database analyzes the change in pressure from the one or more pressure sensors and transmits an alert when the detected pressure change corresponds to the medication input parameters inputted by the user.

In one embodiment, the system further includes one or more medication detection device subgroups stored on the remote database, each of the one or more medication detection device subgroups including one or more of the medication detection devices that are grouped together according to a user-defined parameter, wherein the alert is transmitted when the detected pressure change corresponds to the medication detection device input parameters and medication detection device subgroup parameters inputted by the user.

In a second aspect, a method of tracking inventory of a medication and communicating inventory medication with a includes the steps of: providing one or more medication detecting devices, each of the medication detecting devices having a medication container for receiving a first amount of a medication, a pressure sensing component in sensory contact with the medication portion for measuring a pressure applied by the first amount of medication on the medication portion, an embedded processor in electronic communication with the pressure sensing component and a sensor communication module, providing one or more personal communication devices, the one or more personal communication devices having a display, at least one computer readable storage medium, a device communication module for transmitting and receiving data; and a processor in communication with the display, the at least one computer readable storage medium, and the device communication module; providing a remote database in communication with the one or more pressure sensors and the at least one personal communication device via the sensor communication module of the one or more pressure sensors and the device communication module of the personal communication device, the remote database including a processor and one or more computer readable storage mediums; placing a medication in the medication container of the one or more medication detection devices; receiving user input on the one or more personal communication devices, the user input including data corresponding to one or more alert thresholds, one or more alert contacts, and identifying information of one or more medications placed in the medication container of the one or more medication detection devices; determining an amount of medication in the medication container based on data from the pressure sensing component and user input data identifying the medication; generating an alert if the determined amount of medication corresponds to the data from the user corresponding to the one or more alert thresholds; and transmitting the generated alert to one or more of user-defined alert contacts based on the received user input and the determined amount of medication in the medication container.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
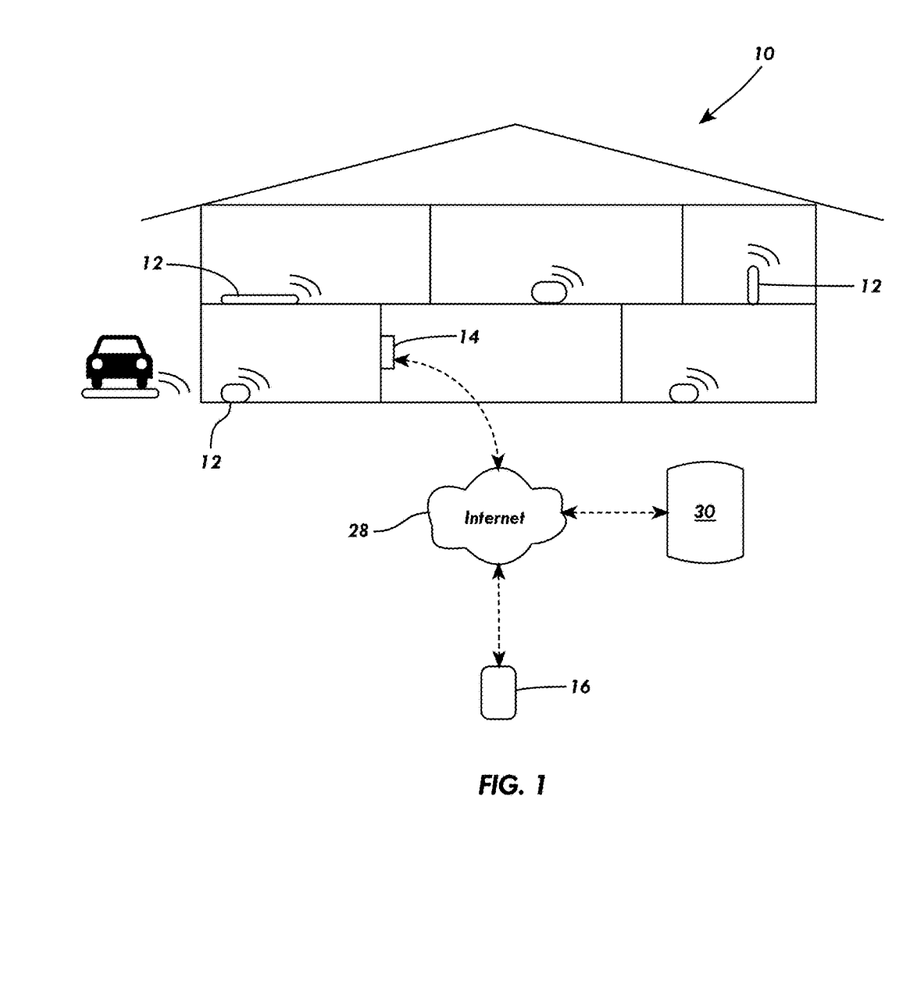
FIG. 1 illustrates a system of linked pressure sensors according to one embodiment of the disclosure.

FIG. 1 shows a basic embodiment of system of linked pressure sensors 10 for communicating with or alerting a user when one or more objects are moved or otherwise displaced. The system of linked pressure sensors 10 includes one or more pressure sensors 12 in communication with a hub 14, with the hub 14 in communication with one or more personal communication devices 16. The system of linked pressure sensors 10 is configured to communicate with a use via the one or more personal communication devices 16 to alert the user of pressure changes detected by the one or more pressure sensors 12, such as by removal or adjustment of an object in contact with the one or more pressure sensors 12.

The one or more pressure sensors 12 are force collector-type pressure sensors for measuring an applied force or pressure over a surface area of the pressure sensor 12. The pressure sensor 12 includes a pressure-measuring component 18 that preferably measures an applied force using one or more of a piezo resistive strain gauge, capacitive, electromagnetic, or other like pressure sensors capable of measuring an applied force over a surface area formed along of a top portion of the pressure sensor 12. The surface area may be substantially flat such that the pressure sensor 12 is capable of receiving an object on the surface area of the pressure sensor 12.

Figure 2:
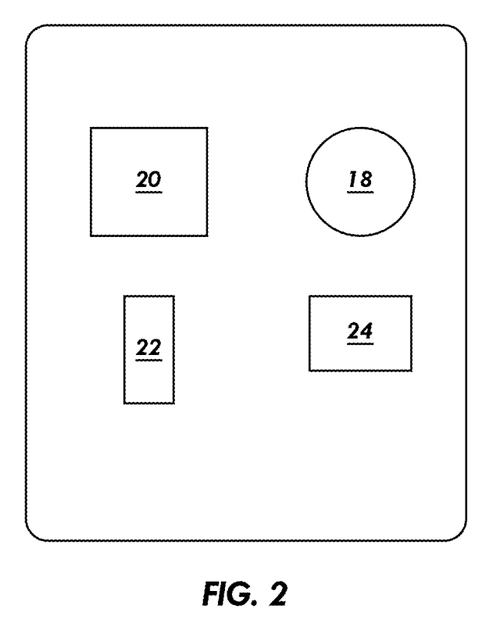
FIG. 2 illustrates a pressure sensor according to one embodiment of the disclosure.

Referring to FIG. 2, the one or more pressure sensors 12 includes an embedded processor 20 in communication with the pressure-measuring component 18. A battery 22 and communication module 24 are also in communication with the embedded processor 20. The communication module 24 is preferably formed of a radio transmitter for wirelessly communicating with the hub 14 of the linked pressure sensor system 10. For example, the radio transmitter may be a transmitter/receiver configured to operate at a relatively low rate of power consumption using short-wavelength radio transmissions, such as Bluetooth® or Bluetooth® low energy (commonly referred to as "Bluetooth® LE" or "Bluetooth Smart®"). Alternatively, the radio transmitter may be configured to transmit/receive over a wireless network within a particular structure, such as WiFi.

The one or more pressure sensors 12 include a housing 26 for containing the various components of the pressure sensor 12. A shape of the housing 26 may vary depending on a desired use of the one or more pressure sensors 12. For example, in one configuration the housing 26 may be a mat or pad such that an object may be placed on top of and in contact with the pressure sensor 12. Alternatively, the housing 26 may be formed into various other shapes capable of receiving and detecting removal of objects in contact with the pressure sensor 12. The housing may be, for example, circular, square, rectangular, or formed into an elongate strip. Further, the housing 16 may include an adhesive or one or more magnets for securing the housing to various surfaces.

Referring again to FIG. 1, the system of linked pressure sensors 10 is preferably located within a structure containing objects of value, such as a dwelling or household. The one or more pressure sensors 12 are placed in contact with the objects of value and communicate with the one or more personal communication devices 16 via the hub 14 when the objects of value are removed or otherwise disturbed.

The one or more personal communication devices 16 preferably include a display, one or more computer readable storage mediums, a processor, and various input/output components. For example, the personal communication device may include components that enable wired communication with an external device or, alternatively, may include wireless communication components. The personal communication device 16 is configured to receive user input, such as through one or more buttons or through a touch screen interface of the display, and is further configured to display information received on the personal communication device 16 on the display. Examples of a suitable personal communication device may include a smartphone, tablet, personal computer, or other like devices.

The hub 14 preferably includes a radio transmitter configured to wirelessly communicate with the communication module 24 of the one or more pressure sensors 12. Further, the hub 14 is in communication with the one or more personal communication devices 16, such as via the Internet. For example, the hub 14 may be in communication with a wireless network of a dwelling in which the hub 14 is installed, thereby enabling the hub 14 to communicate with the one or more personal communication devices 16, such as through the Internet 28. The hub 14 may further include an optional backup communication means, such as a radio transmitter or cellular communications. The hub 14 may be a separate device for specifically communicating with the one or more pressure sensors 12, or alternatively the hub 14 may be comprised of an existing device within a structure, such as an alarm unit.

In one embodiment, the system 10 may be incorporated into an existing home security system. The existing home security system may include existing motion detectors, cameras, and other various home security components. The system 10 may communicate with the existing home security system such that when the one or more pressure sensors 12 detect a change in pressure adjacent the pressure sensors 12 one or more elements of the existing home security system are activated. For example, one or more alarms of the security system may be activated based on detected changes by the pressure sensors 12. Other various security system elements such as cameras may be activated based on changes detected by the pressure sensors 12.

When an object is placed in contact with the pressure sensor 12, the system 10 detects and stores a force measured by each of the one or more pressure sensors 12. Further, each of the one or more pressure sensors 12 may be assigned a name assigned by a user through the personal communication device 16. Data related to the one or more pressure sensors 12 may be stored in a remote database 30 that is in communication with the hub 14 and one or more personal communication devices 16 through the Internet 28. The database 30 may be formed of one or more servers, personal computers, or other similar devices. The database 30 may be located local to the one or more pressure sensors 10 or personal communication device 16 or, alternatively, may be remote from the pressure sensors 10 and personal communication device 16 and communicable with the system via a network, such as over the Internet. The database 30 includes at least one processor and one or more computer readable storage mediums configured to receive and store data from the one or more pressure sensors 12 and personal communication device 16.

Figure 3:
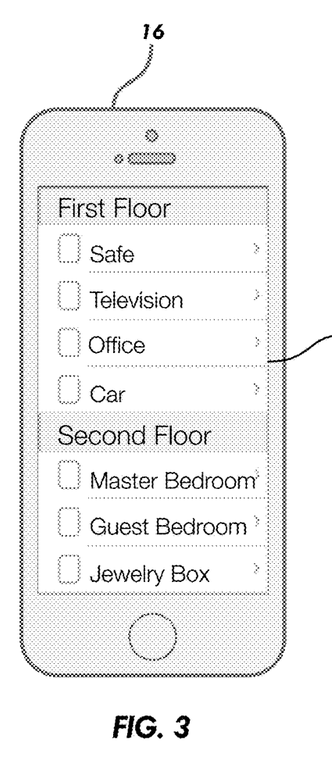
FIGS. 3-5 illustrate a user interface according to one embodiment of the disclosure.
Figure 4:
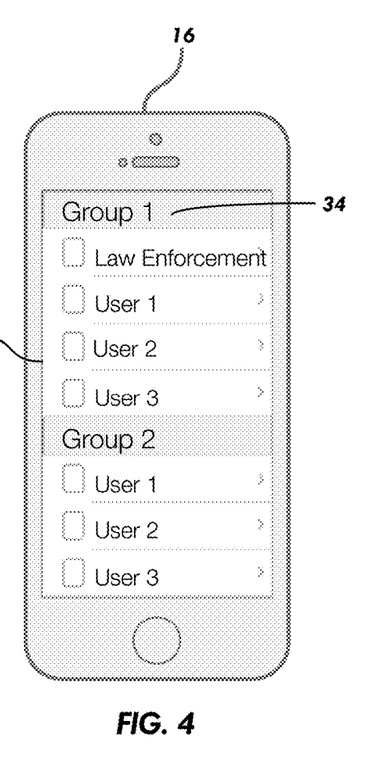
Figure 5:
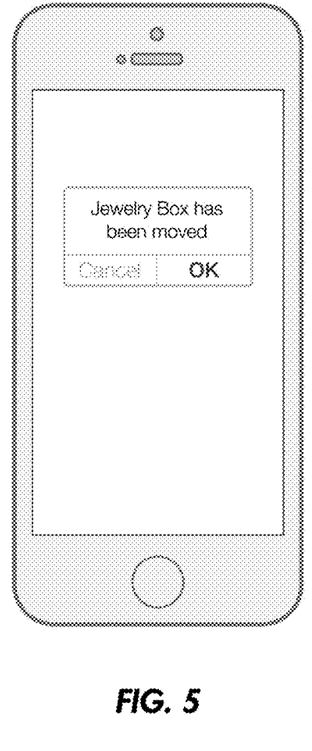

A user may view a status of the one or more pressure sensors and assign various settings to each of the one or more pressure sensors 12 through an interactive user interface 32 on the personal communication device 16 for receiving input from a user and for displaying information related to the one or more pressure sensors, as shown in FIGS. 3-5. Each of the one or more pressure sensors 12 may be assigned a particular indicator based on an object in contact with the pressure sensor or a location of the pressure sensor 12. Further, groups of contacts may be provided by the user for alerting one or more designated contacts in the event that the system 10 detects a change of pressure in the one or more pressures sensors 12 corresponding to removal or adjustment of an object contacting the one or more pressure sensors 12.

FIG. 3 illustrates an exemplary embodiment of the user interface 32 displaying assigned names of the one or more pressure sensors 12 on the personal communication device 16. Each of the pressure sensors 12 may be categorized by group, such as by a location where each pressure sensor is located. Within each group each pressure sensor 12 may be individually named such that a user may identify a location of the one or more pressures sensors 12. Placement of the one or more pressure sensors may include, for example, under a safe or other object, or under a carpet of a particular room to indicate whether a person has entered that particular room. When the housing 26 of the pressure sensor is formed into a mat, the pressure sensor may be placed under one or more tires of a car to indicate whether the car is contacting the pressure sensor 12. In other embodiments, one or more of the pressure sensors 12 may be placed adjacent a container of objects, such as consumable products or parts such that the pressure sensors 12 detect a change in weight of the container of objects corresponding to removal of objects from the container.

The user interface 32 may also a current status of each of the one or more pressure sensors 12, such as whether the pressure sensor 12 is currently detecting an item contacting the pressure sensor 12, as well as additional information such as which contact group is assigned to the particular pressure sensor 12 and a battery life of the pressure sensor 12. A user may activate or deactivate a particular pressure sensor 12 via the user interface 32.

Referring to FIG. 4, a user may designate one or more contact groups in the user interface 32 such that the system 10 contacts designated users within a contact group 34 when changes to an object adjacent the pressure sensor are detected. One or more contact groups 34 may be created wherein each contact group 34 corresponds to particular parties that are to be contacted in the event that one or more pressure sensors 12 of the system 10 detect a change in pressure corresponding to an object adjacent the pressure sensors being removed or otherwise tampered with.

For example, a contact group may include the user and family members, neighbors, or friends of the user and not any emergency services such as a fire department, police, or other authorities. Alternatively, a contact group may include the user and various emergency services such as police, fire, and other emergency services. The system 10 may include various suggested contact groups 34 and further allow users to customize persons listed in each contact group 34 along with when each contact group is to be used.

Each contact group 34 may further be assigned to various of the one or more pressure sensors 12 based on a value or desire to monitor a particular object of value. For example, if the system 10 detects a change in pressure of one of the pressure sensors 12, a first contact group may be alerted, while if a separate pressure sensor 12 detects a change in pressure, a second and different contact group may be alerted.

Figure 6:
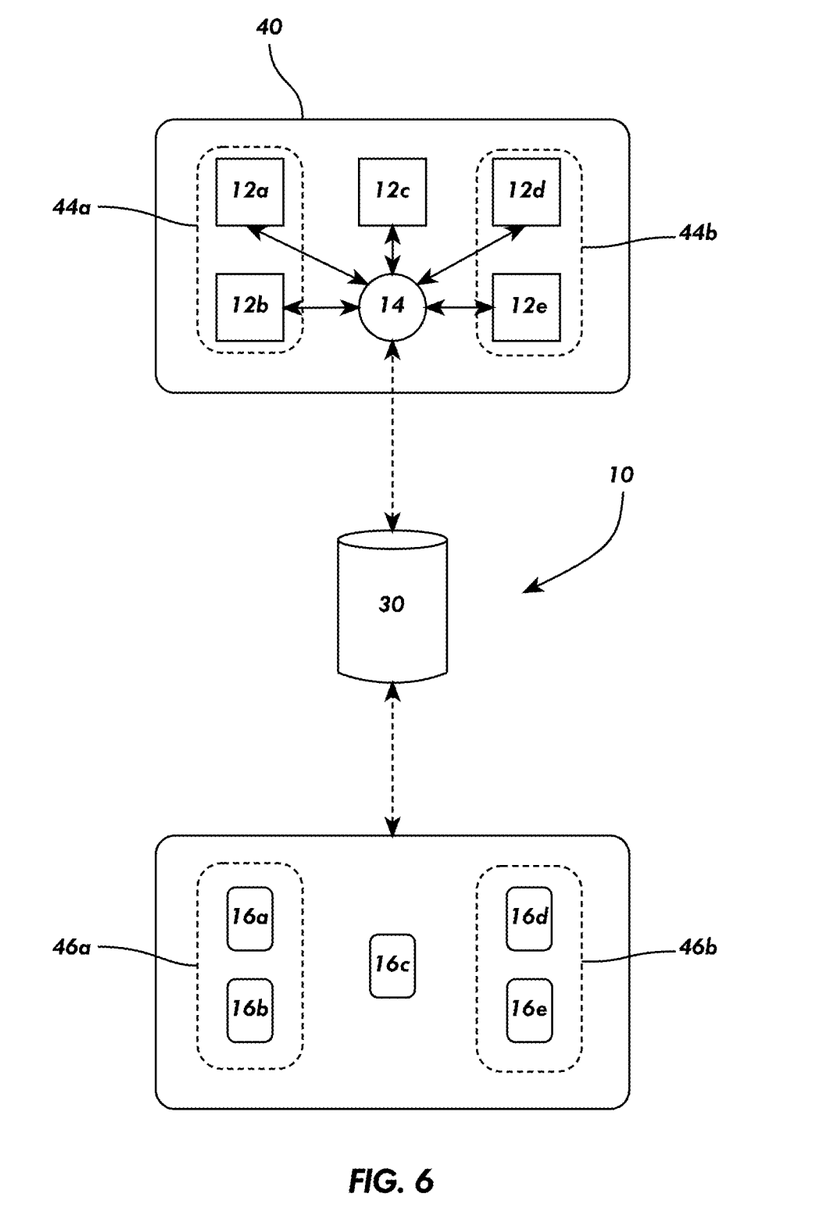
FIG. 6 illustrates a system of linked pressure sensors according to one embodiment of the disclosure.

FIG. 6 illustrates a system of object tracking using a plurality of linked pressure sensors 10. The system includes at least one sensor group 40 that includes a plurality of sensors 12a-12e and at least one personal communication device group 42 that includes a plurality of personal communication devices 16a-16e. The sensor group 40 and personal communication device group 42 are in communication with the remote database 30 via a network, such as over the Internet. One or more of the sensors 12a-12e may be grouped together into sensor subgroups 44a and 44b. Information related to the sensor subgroups 44a and 44b is stored on the remote database 30 such that one or more of the sensors are associated with the subgroups 44a and 44b. Similarly, one or more of the personal communication devices 16a-16e may be grouped together into personal communication device subgroups 46a and 46b.

The plurality of sensors 12a-12e may be assigned to the one or more sensor subgroups 44a and 44b by a user through the user interface 32. Similarly, a user may designate one or more of the personal communication devices 16a-16e into the personal communication device subgroups 46a and 46b using the user interface 32. Identities of one or more sensors 12a-12e are stored on the remote database 30 and associated with a particular subgroup 46a or 46b on the remote database. Identities of the one or more personal communication devices 16a-16e are also stored on the remote database 30 and are associated with one or more personal communication device subgroups 46a or 46b.

Data related to each of the one or more pressure sensors 12a-12e and personal communication devices 16a-16e may be stored on the remote database 30 along with information related to each particular device such as a device identification number and various user-assigned parameters. User-assigned parameters may include information related to each of the one or more pressure sensors 12a-12e such as sensor location, sensor name, one or more subgroups to which the sensor is assigned, items stored on the sensor, threshold warning pressures, and contact groups associated with the sensor such that if a change in pressure is detected members of the sensor's contact group are alerted. A user may create or change the user-assigned parameters using the user interface 32 through one or more of the personal communication devices 16a-16e or other devices in communication with the remote database 30.

The system of linked pressure sensors 10 enables a user to monitor movement of one or more objects of value within a structure such as a household. Further, the system enables a user to designate specific alert settings depending on types of valuables being monitored or the presence of a particular group of people within the structure. The system 10 is customizable to alert various contacts depending on user-selected settings such as which pressure sensor 12 is activated or who is present in the structure in which the system 10 is located.

The one or more pressure sensors 12 are placed throughout a structure at various desired positions, such as adjacent an object or near an entrance to a particular room within a structure such as under a carpet or rug. After placing an object adjacent one or more of the pressure sensors 12, the one or more pressure sensors 12 are activated such that any change in pressure detected by the pressure sensors 12 is alerted by the one or more pressure sensors 12.

To activate one or more of the pressure sensors, a user may input parameters related to each pressure sensor through the user interface 32, such as by using one or more of the personal communication devices 16. The user may enter a name and location of the pressure sensor to be stored on the remote database 30 and associated with the particular pressure sensor. The user may further enter information related to an object stored adjacent to each pressure sensor, such as a known weight of the object, type of object, value of the object, and quantity of objects if more than one object is stored next to an individual pressure sensor. For example, if a box of objects is placed adjacent to one of the pressure sensors such that a weight of the box of objects is detected by the pressure sensor, a user may input information related to a known quantity of objects within the box. In one embodiment, information related to an object stored adjacent to each pressure sensor may be entered automatically, such as by scanning a barcode corresponding to the object with a device in communication with the remote database 30.

After inputting desired information into the remote database 30 for each pressure sensor, an initial weight of the object may be stored on the remote database 30 for each pressure sensor. To establish an initial weight, a user may first place an object on the pressure sensor. Next, using the user interface 32 the user may designate that the pressure detected by the pressure sensor corresponds to the object placed on the pressure sensor. The initial detected pressure is stored on the remote database 30 and associated with the particular pressure sensor. If the user inputted that a known quantity of multiple objects is being placed on the pressure sensor, a weight of each object may be determined based on the detected weight of the multiple objects divided by a number of objects entered by the user.

After inputting information related to an object stored adjacent to each pressure sensor, the user may further input parameters related to a detected change in pressure by the pressure sensor, such parameters being stored on the remote database 30 and associated with a designated pressure sensor. Parameters related to a detected change in pressure may include a desired threshold change in pressure required before an alert is generated on the one or more personal communication devices 16. For example, for an object of high value a user may desire that only a relatively small change in pressure be detected by the one or more pressure sensors for one or more of the personal communication devices to be alerted. Alternatively, a user may desire that a much greater change in pressure be detected, such as by total removal of an object. Similarly, if a plurality of objects is located adjacent to an individual pressure sensor, it may be desired to create an alert only when the pressure sensor detects that only a small number of the original plurality of objects are detected as remaining adjacent the pressures sensor.

The user may further designate one or more contact groups for each pressure sensor or for a group of pressure sensor. Using the user interface 32, the user may select multiple pressure sensors to be formed into sensor subgroups 44a and 44b. For example, multiple pressure sensors within a single room of a structure may be grouped into the same sensor subgroup. Similarly, a user may designate that one or more personal communication devices be formed into one or more personal communication device subgroups 46a and 46b. When a pressure sensor or user device is added to one or more of the sensor subgroups or personal communication device subgroups, information related to that subgroup is stored on the remote database 30 and associated with each of the personal communication devices and pressure sensors in that subgroup.

The pressure sensors detect a pressure exerted on the pressure sensors by objects adjacent to the pressure sensor and transmit a value related to a detected pressure to the remote database 30. If a change in pressure is detected by one or more of the pressure sensors, the changed pressure is analyzed on the remote database 30 to determine whether the change in pressure corresponds to one or more parameters entered by the user indicating that an alert should be generated.

Such change in pressure detected by the one or more pressure sensors 12 is transmitted from the one or more pressure sensors 12 to the remote database 30. The pressure detected by the pressure sensor is then analyzed based on values stored on the remote database 30 for the particular pressure sensor to determine whether an alert should be generated. If an alert should be generated due to a change in pressure exceeding the user-defined parameters, the database 30 transmits an alert to one or more of the personal communication devices that are designated as part of the particular pressure sensor's group. If a defined device subgroup is associated with the particular pressure sensor, an alert is generated to personal communication devices in the device subgroup and an alert is emitted from the one or more personal communication devices of the device subgroup. Further, an alert may be generated only in response to detected pressure changes in multiple pressure sensors, such as a detected change in multiple pressure sensors within a sensor subgroup. Only after each sensor detects a desired change in pressure is an alert transmitted to a personal communication device.

By grouping one or more of the pressure sensors and personal communication devices into subgroups, an alert may only be generated upon pre-designated changes in pressure in desired pressure sensors. For example, an alert may only be generated when each of the pressure sensors assigned to a particular subgroup detects a change in pressure that meets user-defined parameters, such as an object being displaced from each of the pressure sensors of the group. Only upon a detected change in pressure on each of the pressure sensors within the sensor subgroup would an alert be generated and transmitted to one or more personal communication devices.

In one example, one or more of the pressure sensors 12 are formed of a mat placed in a garage or parking area of a structure. When a vehicle is parked on top of the mat, the pressure sensor 12 is activated such and a user may receive an alert on one or more personal communication devices 16 that the sensor is now active.

When the user is away from the structure, such as on a vacation, but anticipates that one or more family members will remain at the structure, the user may designate a contact group consisting only of the user, the user's family members, the user's neighbors, and other non-emergency service contacts. If the vehicle is subsequently moved, such as when the vehicle is driven by a family member residing at the structure while the user is out of town, the pressure sensor detects a change in pressure which is then communicated to the one or more personal communication devices 16 of the user, as well as to the contact group, alerting that the vehicle has been moved.

Alternatively, if the user is away from the structure and does not anticipate that any family members or other known persons will be staying at the structure, the user may designate a contact group consisting of the user and one or more emergency services, such as police. If the pressure sensor 12 detects a change in pressure, an alert is sent to the designated contact group including emergency services.

In another example, one of the one or more pressure sensors 12 is placed adjacent a jewelry box or family heirloom. The pressure sensor 12 is activated such that any change in pressure contacts a designated contact group desired by the user. If the jewelry box or family heirloom are opened or otherwise moved, the one or more pressure sensors 12 detect a change in pressure corresponding to movement of the jewelry box or family heirloom, and one or more contacts of the designated contact group are alerted to movement of the jewelry box or family heirloom.

In yet another example, the one or more pressure sensors 12 may be positioned adjacent a carpet or floor of a room of a structure such that when a person enters the room the one or more pressure sensor 12 detect additional pressure corresponding to a weight of the person entering the room. The pressure sensor 12 may be designated to alert a user either when increased pressure is detected or if pressure is increased and then decreased corresponding to a person stepping on and then stepping off the pressure sensor 12.

Additional pressure sensors 12 may be positioned adjacent objects of value within the particular room. A user may designate contact groups for each pressure sensor 12 within the room. For example, the user may be the only contact alerted when a person enters a particular room, followed by alerting a different contact group if the system 10 detects removal of objects within the room.

Medication Inventory/Tracking

Figure 7:
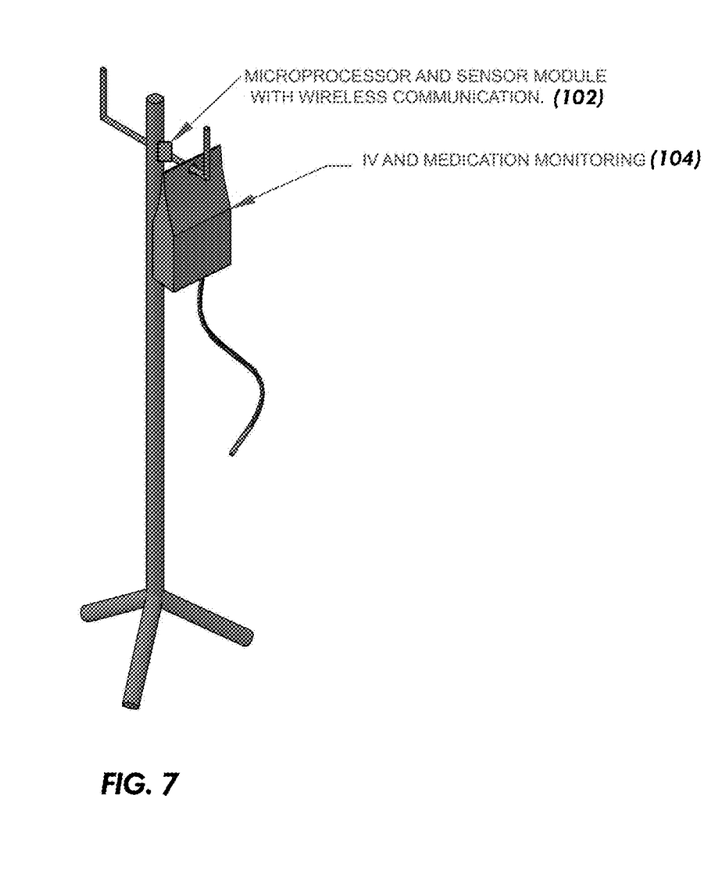
FIGS. 7 and 8 illustrate one or more pressure sensors for tracking an amount of medication available to a patient according to one embodiment of the present disclosure.
Figure 8:
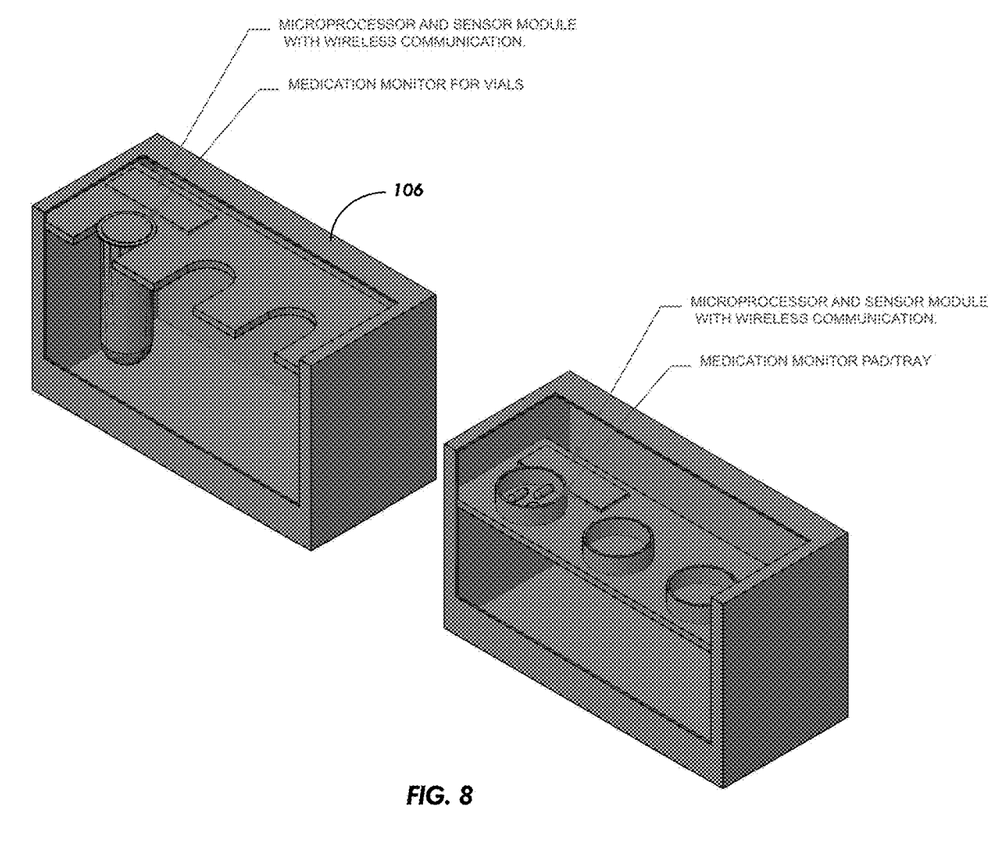

In one embodiment, a system and method for tracking medication inventory or quantity using one or more linked pressure sensors is provided. As shown in FIGS. 7 and 8, a pressure sensor 102 is located adjacent to a container or other area where a patient's medication is located to detect an amount of medication within the container and determine when a medication is running low or has been depleted. The pressure sensor 102 is in communication with a remote database for alerting that a supply of medication is running low or has been exhausted.

The system and method for tracking medication inventory or quantity using one or more linked pressure sensors may be employed in a hospital or commercial setting (such as a retirement community or other healthcare entity) or in a home environment. FIG. 7 illustrates an exemplary embodiment that includes the pressure sensor 102 mounted adjacent to a medication container such as a medication bag 104 containing an intravenous solution. The pressure sensor 102 includes a processor and a wireless communication module for communicating with a database that is remote from the pressure sensor 102. The pressure sensor 102 may include components as discussed above and illustrated in FIG. 2 The pressure sensor 102 may also include a local memory unit for storing one or more values related to a force detected by the pressure sensor 102.

FIG. 8 illustrates additional embodiments including a base 106 that includes an embedded processor and pressure sensor for detecting force exerted by a medication, such as medication within a vial or other container. The pressure sensor is positioned adjacent to a medication vial support, or adjacent to a container for holding one or more pills such that the pressure detector senses a force exerted by the medication. A communications module is included with the base 106 for communicating with a database that is remote from the pressure sensor.

The pressure sensor is in communication with one or more personal communication devices via a database, as described in the present disclosure. The database may receive data from the personal communication devices to establish a threshold for signaling an alert that a medication is running low or has been exhausted. Further, a quantity of medication available may be determined based on a force detected by the pressure sensor and data stored on the database or stored on memory of the processor in communication with the processor.

When a user desires to track an amount of medication available adjacent the pressure sensor, the user, via a user interface on the personal communication device, may input a type of medication. Additional data may be stored on or retrieved by the database such as whether the medication is a solid or liquid, dosage amounts of the medication, and other data related to a particular medication. The user may also input information such as a number of pills or a volume of medication positioned adjacent the pressure sensor.

The user may assign various contact groups to types of medications depending on an appropriate contact group to be alerted. For example, various types of medications may require refilling from different sources, or different healthcare providers may need to be alerted based on an amount of a particular medication available. The user assigned contact groups may be alerted when one or more defined conditions exist as explained above.

Additional data related to a container of the medication may be stored on or retrieved by the database, such as known or estimated weights of an empty medication container. For example, empty intravenous bag weights of various volumes may be stored on the database, or weights of other empty medication containers.

Using data related to the type of medication and the amount of medication, the database may determine a per-unit force of the medication to determine an amount of medication available and to determine when a medication is running low. For example, using known information such as a weight of a container and an amount of medication, the quantity of medication is determined by the database and as the force detected by the pressure sensor changes related to medication being consumed by a patient. When an amount of medication reaches a user-defined or pre-determined quantity, an alert may be transmitted to one or more of the personal devices.

Figure 9:
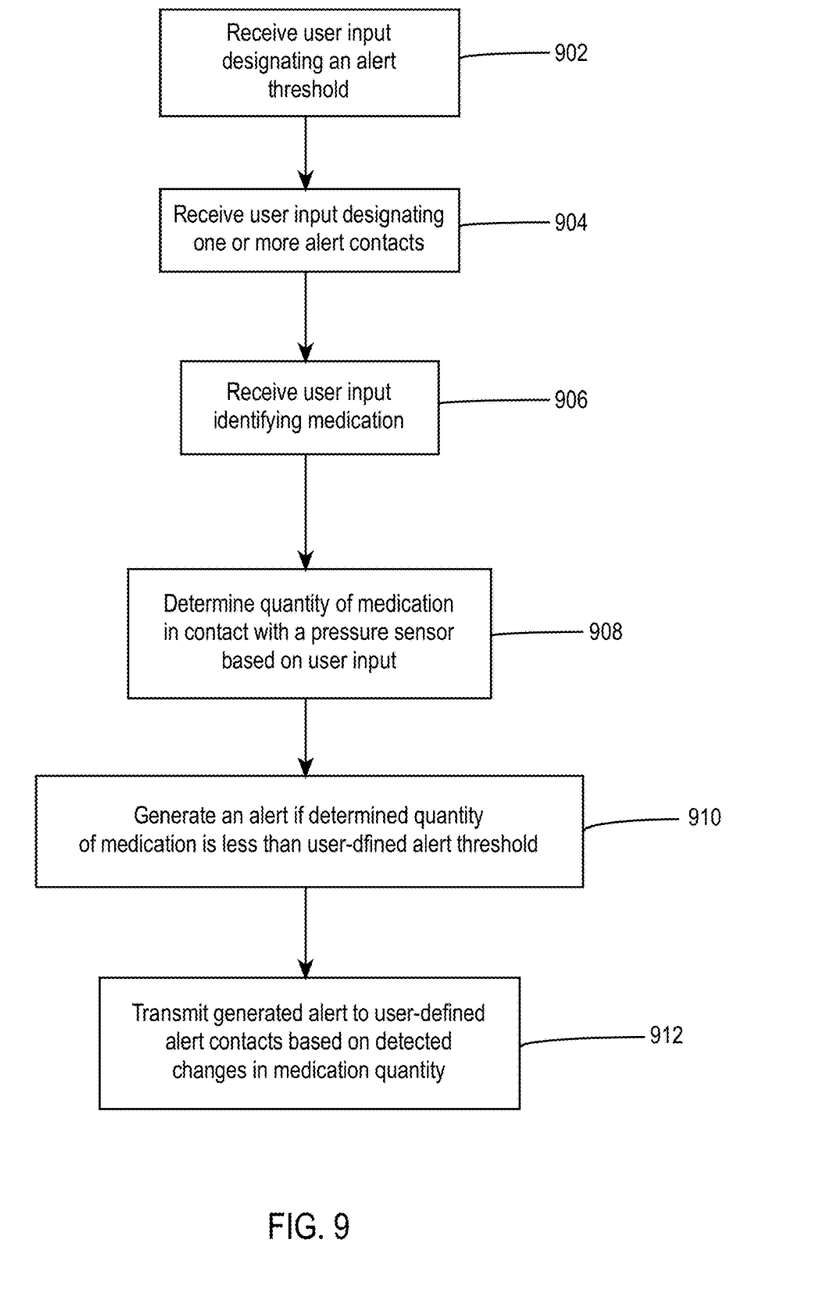
FIG. 9 is a flow chart of a method of tracking a quantity of medication according to one embodiment of the present disclosure.

Referring to FIG. 9, a user may input data corresponding to one or more alert thresholds at step 902, such as by identifying a quantity or amount of medication detected on the pressure sensor 102 before an alert is generated. For example, a first threshold may correspond to an amount of medication detected as low, while a second threshold may correspond to a lower amount of medication or a determination that medication has been depleted. At step 904, a user may further input one or more alert contacts. Each alert contact may correspond to a contact that is alerted when a threshold is crossed. One contact may correspond to a first threshold amount, while other contacts may correspond to a second and other threshold amounts. At step 906, a user inputs additional information such as identifying information of a medication (type of medication, amount of medication, etc.).

A quantity of medication is determined at step 908 based on data from the pressure sensor 102 and user input identifying the medication. For example, if the user input includes a number of pills of a medication, a pressure change corresponding to each pill may be determined such that removal of medication may be detected. For a liquid medication, a user may input information such as a volume of medication or a dose size of the medication.

If a quantity of medication is determined to be less than one or more of the threshold amounts, an alert is generated at step 910. The alert may be generated at each of the one or more designated thresholds. At step 912, the alert is transmitted to one or more user-defined alert contacts based on detected changes in a quantity of medication and the user-defined information inputted at steps 902-906.

The system of the present disclosure also provides a method of tracking objects using the one or more pressure sensors and generating an alert if one or more user defined events occurs. The method includes activating one or more of the pressure sensors by inputting one or more parameters related to each pressure sensors and designating one or more sensor subgroups and device subgroups, and further includes providing an alert to one or more personal communication devices in communication with the pressure sensors via the remote database 30 when a user defined event occurs. A user defined event may be a detected pressure change in one or more of the pressure sensors wherein the pressure change exceeds a designated threshold. Similarly, a user defined event may occur a detected change in a plurality of the one or more pressure sensors.

The system and method of object tracking using a plurality of linked pressure sensors allows a user to define various parameters related to one or more pressure sensors and may generate an alert only based upon a pre-defined set of user parameters. The system allows objects across multiple pressure sensors to be tracked using the pressure sensors in communication with the personal communication devices through the remote database, and allows a user to customize an event that results in an alert being generated. The system is suitable for tracking objects within a household or, alternatively, may be used in a commercial or industrial environment by tracking a location of one or more assets or inventory. The system further allows customized groups of users to be alerted to designated changes in pressure on each of the pressure sensors, and further allows pressure sensors to be grouped such that an alert is generated only when a desired change in pressure occurs in each pressure sensor of a desired group.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A system for tracking an inventory of medication, the system comprising:
   one or more medication detecting devices, each of the medication detecting devices including:
      a medication container for receiving a first amount of a medication;
      a pressure sensor including a pressure sensing portion in sensory contact with the medication portion for measuring a pressure applied by the first amount of medication on the medication portion;
      an embedded processor in electronic communication with the pressure sensing component and a sensor communication module;
   one or more personal communication devices, the one or more personal communication devices including:
      a display,
      at least one computer readable storage medium,
      a device communication component; and
      a processor in communication with the display, the at least one computer readable storage medium, and the device communication module;
   a remote database in communication with the one or more medication detecting devices and the one or more personal communication device via the sensor communication module of the one or more medication detecting devices and the device communication module of the personal communication device, the remote database including a processor and one or more computer readable storage mediums;
   an interactive user interface displayed on the display of the personal communication device for receiving one or more medication parameters from a user corresponding to a change in pressure detected by the pressure sensing component of each of the one or more medication detecting devices and for displaying information related to the one or more medication detecting devices;
   wherein when one of the one or more medication detecting devices detects a pressure change on the pressure sensor, the detected change of pressure is transmitted to the remote database, wherein the remote database processor analyzes the change in pressure from the one or more medication detecting devices and transmits an alert when the detected pressure change corresponds to the medication input parameters inputted by the user.

2. The system of claim 1, further comprising one or more medication detection device subgroups stored on the remote database, each of the one or more medication detection device subgroups including one or more of the medication detection devices that are grouped together according to a user-defined parameter, wherein the alert is transmitted when the detected pressure change corresponds to the medication detection device input parameters and medication detection device subgroup parameters inputted by the user.

3. A method of tracking inventory of a medication and communicating inventory medication with a user, the method comprising the steps of:
   providing one or more medication detecting devices, each of the medication detecting devices including:
      a medication container for receiving a first amount of a medication;

a pressure sensing component in sensory contact with the medication portion for measuring a pressure applied by the first amount of medication on the medication portion;

an embedded processor in electronic communication with the pressure sensing component and a sensor communication module;

providing one or more personal communication devices, the one or more personal communication devices including:

a display, at least one computer readable storage medium, a device communication module for transmitting and receiving data; and a processor in communication with the display, the at least one computer readable storage medium, and the device communication module;

providing a remote database in communication with the one or more medication detecting devices and the one or more personal communication device via the sensor communication module of the one or more medication detecting devices and the device communication module of the personal communication device, the remote database including a processor and one or more computer readable storage mediums;

placing a medication in the medication container of the one or more medication detection devices;

receiving user input on the one or more personal communication devices, the user input including data corresponding to one or more alert thresholds, one or more alert contacts, and identifying information of one or more medications placed in the medication container of the one or more medication detection devices;

determining an amount of medication in the medication container based on data from the pressure sensing component and user input data identifying the medication;

generating an alert if the determined amount of medication corresponds to the data from the user corresponding to the one or more alert thresholds;

transmitting the generated alert to one or more of user-defined alert contacts based on the received user input and the determined amount of medication in the medication container.

* * * * *